(12) United States Patent
Richter

(10) Patent No.: US 8,448,523 B2
(45) Date of Patent: May 28, 2013

(54) DEVICE AND METHOD FOR DETERMINING AT LEAST ONE FLOW PARAMETER

(75) Inventor: Martin Richter, Munich (DE)

(73) Assignee: Fraunhofer-Gesellschaft zur Foerderung der Angewandten Forschung E.V., Munich (DE)

( * ) Notice: Subject to any disclaimer, the term of this patent is extended or adjusted under 35 U.S.C. 154(b) by 253 days.

(21) Appl. No.: 13/052,452

(22) Filed: Mar. 21, 2011

(65) Prior Publication Data

US 2011/0224603 A1 Sep. 15, 2011

Related U.S. Application Data

(63) Continuation of application No. PCT/EP2008/007988, filed on Sep. 22, 2008.

(51) Int. Cl.
*G01F 1/00* (2006.01)
(52) U.S. Cl.
USPC .................................................. 73/861
(58) Field of Classification Search
USPC ................... 73/861, 861.58, 861.57
See application file for complete search history.

(56) References Cited

U.S. PATENT DOCUMENTS

| | | | | |
|---|---|---|---|---|
| 4,221,134 A * | 9/1980 | Ekstrom, Jr. | ................. | 73/721 |
| 4,994,035 A | 2/1991 | Mokros | | |
| 5,720,721 A | 2/1998 | Dumas et al. | | |
| 6,338,279 B1 * | 1/2002 | Tsataros | ................. | 73/861.56 |
| 6,443,014 B1 * | 9/2002 | Richter | ................. | 73/715 |
| 6,591,674 B2 * | 7/2003 | Gehman et al. | ................. | 73/204.22 |
| 2004/0127844 A1 | 7/2004 | Flaherty | | |
| 2005/0267413 A1 | 12/2005 | Wang et al. | | |
| 2007/0151346 A1 | 7/2007 | Malmstrom et al. | | |

FOREIGN PATENT DOCUMENTS

| | | |
|---|---|---|
| DE | 4308313 A1 | 9/1994 |
| EP | 0401524 A2 | 5/1990 |
| EP | 1769738 A1 | 4/2007 |

(Continued)

OTHER PUBLICATIONS

English translation of the Int'l Preliminary Report on Patentablility, dated Mar. 22, 2011, in related PCT application No. PCT/EP2008/007988, 9 pages.

(Continued)

*Primary Examiner* — Jewel V Thompson
(74) *Attorney, Agent, or Firm* — Michael A. Glenn; Glenn Patent Group

(57) ABSTRACT

A device for detecting at least one flow parameter includes a fluidic series connection of a first flow restriction, a first measurement area, a second flow restriction, and a second measurement area. A first sensor is provided for detecting a quantitative first measure of a pressure existing in the first measurement area. A second sensor is provided for detecting a quantitative second measure of a pressure existing in the second measurement area. An evaluator is provided which is configured to determine, while using the measures detected by the first and second sensors, a flow rate of a fluid flowing through the series connection, and/or to determine whether there is an occlusion of the first flow restriction, of the second flow restriction, or of a fluid area adjoining the second measurement area.

25 Claims, 7 Drawing Sheets

FOREIGN PATENT DOCUMENTS

| | | |
|---|---|---|
| EP | 1772162 A1 | 4/2007 |
| EP | 1818664 A1 | 8/2007 |
| JP | 2001-503146 | 3/2001 |
| JP | 2004-531314 | 10/2004 |
| JP | 2008-501117 | 1/2008 |
| WO | WO96/03168 | 2/1996 |
| WO | WO2005/119181 A1 | 12/2005 |

OTHER PUBLICATIONS

English translation of the Written Opinion, dated Jun. 18, 2009, in related PCT application No. PCT/EP2008/007988, 8 pages.

Int'l Search Report, dated Jun. 18, 2009, in related PCT application No. PCT/EP2008/007988, 17 pages.

* cited by examiner

DEVICE AND METHOD FOR DETERMINING AT LEAST ONE FLOW PARAMETER

CROSS-REFERENCE TO RELATED APPLICATIONS

This application is a continuation of copending International Application No. PCT/EP2008/007988, filed Sep. 22, 2008, which is incorporated herein by reference in its entirety.

BACKGROUND OF THE INVENTION

Embodiments of the present invention relate to devices and methods for detecting at least one flow parameter, and in particular to devices and methods that are suitable for determining a flow rate and/or an occlusion of a flow restriction.

Embodiments of the invention are suited in particular for utilization in the field of medical technology, and, in medical technology, in particular for utilization with infusions, an infusion generally being understood to mean the supply of a liquid to the venous or arterial part of the circulation of a living being.

BACKGROUND OF THE INVENTION

The range of tasks of infusion therapy is large and essentially lies in the fields of supplying carriers of calories in the case of artificial feeding, of supplying medicines, of regulating the electrolyte balance and the acid-base equilibrium, of supplying liquid for forced excretion of toxins via the kidneys, for example in the event of poisoning by sleeping drugs and the like. Within a hospital, infusions are mainly used in intensive care medicine, in admission and emergency care, in operations, in deliveries, in baby and child care, in functional diagnostics as well as in regular care. An infusion may be performed manually or by using infusion devices.

For selecting the expedient infusion method, the infusion rate that may be used, the infusion duration, the dosing accuracy and the application method that may be used are critical. Most frequent use is made of the conventional, manual infusion method, which is gravity infusion with few requirements placed on the dosing accuracy and the dosing rate. An architecture for such a diffusion is schematically depicted in FIG. 8. The supply of liquid is effected only by the hydrostatic pressure gradient between a patient 1 and an infusion solution filled into a bottle 2.

Assistance is possibly provided by compressing the infusion solution, which may be referred to as a manual pressure infusion. A drip chamber 3 and a roller tubing clamp 4 are provided in the fluid path between the infusion bottle 2 and the patient 1.

In such an arrangement, it is difficult to dose the infusion since the infusion rate, i.e. the velocity of the supply of liquid, can only be regulated manually by closing or opening the roller tubing clamp 4, as is schematically depicted in FIG. 9, which shows three states of a roller tubing clamp; in the left-hand illustration, a fluid tubing 5 is completely pinched off by a roller 6 of the roller tubing clamp, in the central illustration, the fluid tubing 5 is partly pinched off by the roller, and in the right-hand illustration, the fluid tubing 5 is not pinched off by the roller. A corresponding guide 7 is provided which enables the roller 6 to move in the manner shown in FIG. 9 so as to realize different pinch-off states of the fluid tubing 5.

The infusion rate is dependent on a multitude of factors which are hardly or not at all eliminated by a roller tubing clamp. Such factors are, among others, the molding and manufacturing quality of the drip tube within the drip chamber 3 of the infusion set, the drop formation rate, the stability of the delivery pressure, the physical properties of the infusion solution, and the ambient conditions. On account of said factors, only low levels of delivery accuracy of ±20% may be achieved with manual infusion systems, deviations of ±50% being not uncommon.

On account of this low level of delivery accuracy, gravity infusion is applied when infusion therapy allows it. In addition, the physical preconditions for gravity infusion, such as pressure and delivery rate, also need to be met. With gravity infusion, the delivery rate and a catheter closure are measured only manually by counting the drops in the drip chamber. With very low dosing rates, very long observation times may be used in order to recognize a closure. In addition, production of a drip chamber is a cost factor.

By employing infusion devices that use syringe pumps, for example, infusion therapy may be improved in terms of an increase in the infusion rate, an increase in the dosing accuracy, and a guarantee of constant delivery with long-term infusion therapies. On account of said advantages of infusion devices, the spectrum of treatment of infusion therapies may be expanded. In infusions using syringe pumps, the delivery volume is measured only indirectly via the advancement of the syringe motor. The dosing rate is not measured directly, which represents a safety risk. In infusions using syringe pumps, a catheter closure is typically detected by detecting the increase in the motor current. Particularly with small delivery volumes, a closure of the catheter is detected only after long delay times of up to one hour.

A device for supplying fluid to a patient has been known from U.S. 2004/0127844 A1. The device comprises a dispenser, a fluid conduit having an output port suited for coupling to a needle, for example, and a flow state sensor in the flow conduit between the dispenser and the output port. The processor is programmed to cause a fluid to flow to the outlet port. The flow state sensor monitors flow conditions in the fluid path that may occur during operation in order to ensure that the fluid is supplied as intended. The flow state sensor has a diaphragm which partly limits a fluid chamber, so that a pressure within the fluid chamber may be qualitatively evaluated by means of a deflection of the diaphragm. Quantitative measurement of a pressure or determination of a flow rate do not take place.

From U.S. 2007/0151346 A1, an optical pressure monitoring system is known which comprises a conduit from an infusion set as well as an optical signal sensor which is arranged to detect changes in the diameter of the conduit and to thereby determine pressure changes within the conduit. One such sensor may be arranged upstream and downstream from a rotor pump, respectively. A comparable arrangement is also described in U.S. Pat. No. 5,720,721.

U.S. Pat. No. 4,994,035, EP-A1-1769738, EP-A1-1818664 and EP-A2-0401524 each describe sensors for determining pressures in the fluid path of microdosing devices, such as infusion conduits, for example.

SUMMARY

According to an embodiment, a device for determining at least one flow parameter may have: a fluidic series connection having, in this order, a first flow restriction, a first measurement area, a second flow restriction, and a second measurement area; a first sensor for detecting a quantitative first measure of the pressure in the first measurement area; a second sensor for detecting a second quantitative measure of the pressure in the second measurement area; and an evaluator configured to determine, while using the measures detected by the first and second sensors, whether there is an occlusion of the first flow restriction, of the second flow restriction or of a fluid area adjoining the second measurement area.

According to another embodiment, a fluidic module for a device as claimed in claim 12 may have: a module body having a structured module body surface; and a diaphragm mounted on the module body and defining a fluid area together with the structured module body surface, the fluid area having a first flow restriction, a first measurement chamber adjoining the first flow restriction, a second flow restriction adjoining the first measurement chamber, and a second measurement chamber adjoining the second flow restriction.

According to another embodiment, a detection module for a device as claimed in claim 13, which may be fitted onto the elastic tubing may have: a first clamping device for clamping the detection module onto the elastic tubing at a first position alongside the elastic tubing; a second clamping device for clamping the detection module onto the elastic tubing at a second position alongside the elastic tubing, said second position being spaced apart from the first position, the first and second clamping devices being configured to compress the elastic tubing in a defined manner in each case so as to define the first and second flow restrictions; the first sensor, which is configured to detect a measure of the pressure existing between the first and second flow restrictions within the elastic tubing; and the second sensor, which is configured to measure a measure of the pressure existing within a tubing area arranged on a side of the second flow restriction that faces away from the first flow restriction.

According to another embodiment, a method of determining at least one flow parameter may have the steps of: introducing a fluid into a fluidic series connection having, in this order, a first flow restriction, a first measurement area, a second flow restriction, and a second measurement area, detecting a quantitative first measure of a pressure in the first measurement area, and detecting a quantitative second measure of a pressure in the second measurement area; and determining whether an occlusion of the first flow restriction, of the second flow restriction or of a fluid area adjoining the second measurement area is present while using the detected quantitative first and second measures.

Another embodiment may have an infusion apparatus having a device as claimed in claim 1.

Another embodiment may have an infusion apparatus having a fluidic module as claimed in claim 14.

Another embodiment may have an infusion apparatus having a detection module as claimed in claim 17.

Embodiments of the invention provide a device for determining at least one flow parameter, comprising:

a fluidic series connection of a first flow restriction, a first measurement area, a second flow restriction, and a second measurement area;

a first sensor for detecting a first quantitative measure of a pressure in the first measurement area;

a second sensor for detecting a second quantitative measure of a pressure in the second measurement area; and an evaluation means configured to determine, while using the measures detected by the first and second sensors, a flow rate of a fluid flowing through the series connection, and/or to determine whether there is an occlusion of the first flow restriction, of the second flow restriction or of a fluid area adjoining the second measurement area.

Embodiments of the invention provide a method of determining at least one flow parameter, comprising:

introducing a fluid into a fluidic series connection of a first flow restriction, of a first measurement area, of a second flow restriction, and of a second measurement area, detecting a first quantitative measure of a pressure in the first measurement area, and detecting a second quantitative measure of a pressure in the second measurement area;

determining a flow rate of the fluid and/or determining whether an occlusion of the first flow restriction, of the second flow restriction or of a fluid area adjoining the second measurement area is present while using the detected quantitative measures.

Embodiments of the invention further provide a fluidic module and a detection module for a corresponding device.

Embodiments of the invention are based on the finding that utilization of two flow restrictions and of two pressure sensors arranged downstream from the flow restrictions in each case enables both determining a flow rate of a fluid flowing through a corresponding fluidic structure and reliably detecting occlusions of the respective flow restrictions or of a fluid area following the second measurement area.

"Flow restriction" herein is understood to mean a flow restriction which has a defined flow resistance, i.e. known geometric dimensions that may be used for determining the dosing rate. In embodiments of the invention, the flow restrictions are configured such that with flows occurring during normal operation (i.e. without any occlusions), a pressure drop occurs which causes the pressure in the second measurement area to be smaller than the pressure in the first measurement area.

In embodiments of the invention, the measurement areas each have diaphragm sections that are deflected by the pressure existing in the measurement areas, so that the pressure-dependent positions of the diaphragms located downstream from a flow restriction with a defined flow resistance may be measured.

In embodiments of the invention, those parts of the device that come into contact with the flowing fluid may be configured as disposable, or single-use, parts that may be exchangably coupled to the remaining components. Said single-use parts may be configured as plastic parts involving very low cost. By means of the inventive approach, drip chambers may become superfluous, so that they may be omitted, so that cost saving in terms of the single-use parts may result as compared to conventional single-use infusion sets.

Embodiments of the invention enable detecting a closure without any delay, even at low infusion rates, in particular when the inventive device is provided immediately upstream from a patient port, for example in the form of a cannula. In embodiments of the invention, an alarm function may be provided so as to set off an alarm upon detection of an occlusion. In embodiments of the invention, the infusion rate may be measured, which is considerably more precise as compared to a drop-counting method; a display may be provided which indicates the flow rate determined. By means of a corresponding display, a nurse may further be enabled to accurately adjust the infusion rate by means of a roller tubing clamp, whereby the dosing accuracy may clearly increase.

With the inventive approach, the cost of the single-use part may be clearly reduced as compared to syringe infusion methods. In embodiments of the invention, the evaluation means may communicate with a pumping device, for example a syringe pump, so as to control same to achieve a desired flow rate. In addition, the evaluation means may be configured to detect and/or indicate any faults that may occur. For example, a catheter closure may be detected without a delay even at low infusion rates. The infusion rate can be measured directly, so that the dosing rate may be readjusted accordingly by the pumping device, such as the syringe pump, in order to achieve a desired dosing rate. In addition, in embodiments, the evaluation means may also detect when the pumping means fails entirely.

Of course, embodiments of the inventive devices and methods may also be employed—in addition to medical technology—in other fields where a fluid needs to flow at a defined flow rate.

BRIEF DESCRIPTION OF THE DRAWINGS

Embodiments of the present invention will be detailed subsequently referring to the appended drawings, in which.

DETAILED DESCRIPTION OF THE INVENTION

Figure 1:
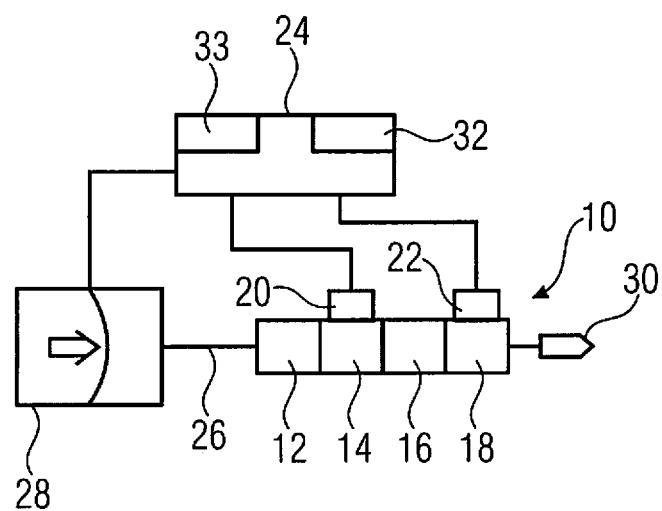
FIG. 1 shows a schematic representation of an embodiment of an inventive device.

FIG. 1 schematically shows an embodiment of a device for detecting at least one flow parameter. The device comprises a series connection 10 of a plurality of fluid areas, which comprises a first fluid restriction 12, a first measurement area 14 connected downstream, in the flow direction, from the first fluid restriction 12, a second fluid restriction 16 connected downstream, in the flow direction, from the first measurement area 14, and a second measurement area 18 connected downstream, in the flow direction, from the second fluid restriction 16. The first measurement area 14 has a first sensor 20 associated with it, and the second measurement area 18 has a second sensor 22 associated with it. The sensors 20 and 22 are configured to detect a measure of the pressure that exists in the associated measurement areas 14 and 18, for example by detecting the deflection of a respective diaphragm that adjoins the measurement area 14 and the measurement area 18. The sensors 20 and 22 are communicatively connected (in a wireless or wired manner) to an evaluation means 24, which may be implemented by a microprocessor means, an ASIC (application-specific integrated circuit) or the like, as is obvious to a person skilled in the art.

The series connection 10 is fluidically connected into a fluid conduit 26 which fluidically connects a pumping means 28 to a cannula 30. The cannula 30 may be an infusion needle, for example, for providing an infusion for a patient. The evaluation means receives the measures of the pressure in the measurement areas 14 and 18 from the sensors 20 and 22, and may be configured to determine, on the basis thereof, a rate of flow through the series connection 10 and, thus, through the fluid conduit 26. The evaluation means 24 may further be configured to establish occlusion conditions on the basis of the output signals of the sensors 20 and 22, as will be explained in more detail below with reference to FIG. 5. The evaluation means 24 may have a display device 32 for displaying the flow rate and/or an occlusion. The evaluation means 24 may further comprise an alarm means (not shown) for indicating an occlusion.

As is shown in FIG. 1, the evaluation means 24 may further be communicatively connected (either in a wireless or in a wired manner) to the pumping means 28 in order to control the pumping means 28 while using the determined rate of flow through the fluid conduit 26, so as to achieve a desired rate of flow through the fluid conduit 26 and, thus, the cannula 30. Alternatively, a roller tubing clamp (not shown in FIG. 1) might be provided via which a user may set a desired flow rate while using the indicated flow rate that has been determined.

Figure 2:
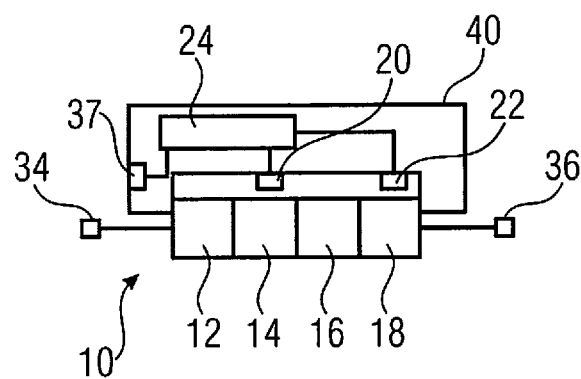
FIG. 2 shows a schematic representation of an alternative embodiment.

FIG. 2 shows a schematic view of an embodiment of a device for determining at least one flow parameter, wherein the parts that come into contact with the flowing fluid are designed as single-use articles. Said parts are the fluidic series connection 10, which has fluidic ports 34 and 36 provided at its inlet end and outlet end, said fluidic ports serving to connect the series connection 10 e.g. into a fluid conduit between a pumping means and a patient.

The single-use module described which comprises the parts that come into contact with the flowing fluid may be exchangeably coupled to a detector module 40 comprising the sensors 20 and 22 that are coupled to the evaluation means 24. The single-use module and the detector module 40 are connectable in a suitable manner such that the sensors 20 and 22 are properly positioned with regard to the measurement areas 14 and 18 so as to be able to detect a measure of the pressure existing in the measurement areas. Corresponding alignment means for achieving such an arrangement may be provided both at the detector module and at the single-use module which comprises the fluid areas. In addition, suitable quick-connection means such as screws or clamps may be provided for exchangeably attaching the modules to one another.

In embodiments of the invention, the measure of the pressure in the measurement areas is detected by measuring the pressure-dependent positions at two deflected diaphragms, each of which is located downstream from a flow restriction having a defined flow resistance. An embodiment of a corresponding module comprising a corresponding series connection of fluid areas is shown in FIGS. 3a and 3b, FIG. 3a depicting a cross-sectional representation, and FIG. 3b depicting a top view.

Figure 3A:
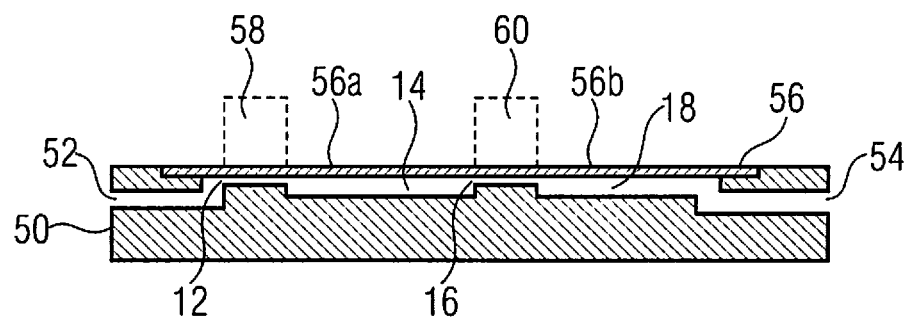
FIGS. 3a, 3b show schematic representations of an embodiment of an inventive fluidic module.

The fluidic module shown in FIG. 3a comprises a module body 50 consisting of one piece and having a supply conduit 52 and a discharge conduit 54 formed therein. In addition, the top surface of the module body 50 is structured to define, along with a diaphragm 56, the first flow restriction 12, the first measurement area 14, the second flow restriction 16, and the second measurement area 18. As is shown in FIG. 3a, the diaphragm 56 may be inserted into a recess in the top surface of the module body 50. Diaphragm sections 56a and 56b of the diaphragm 56 that are arranged above the measurement areas 14 and 18 are deflectable in dependence on a pressure that exists in the measurement areas 14 and 18, so that a measure of the pressure within the measuring chamber 14 may be detected by detecting the position of the diaphragm section 56a, and so that a measure of the pressure within the measuring chamber 18 may be detected by detecting the position of the diaphragm section 56b. To prevent deflection of the diaphragm in the area of the flow restrictions 12 and 16 and, thus, to ensure a constant flow resistance of the flow restrictions, the detector module to which the fluidic module shown in FIG. 3a is exchangeably connected may comprise hold-up elements which in FIG. 3a are indicated by dashed lines and are designated by reference numerals 58 and 60. Alternatively, the diaphragms may be deflectable in the area of the flow restrictions 12 and 16, so that the flow cross-section of the flow restrictions is dependent on pressure, which has the advantage that given the same pressure drop, the flow area may be extended toward higher flows.

Figure 3B:
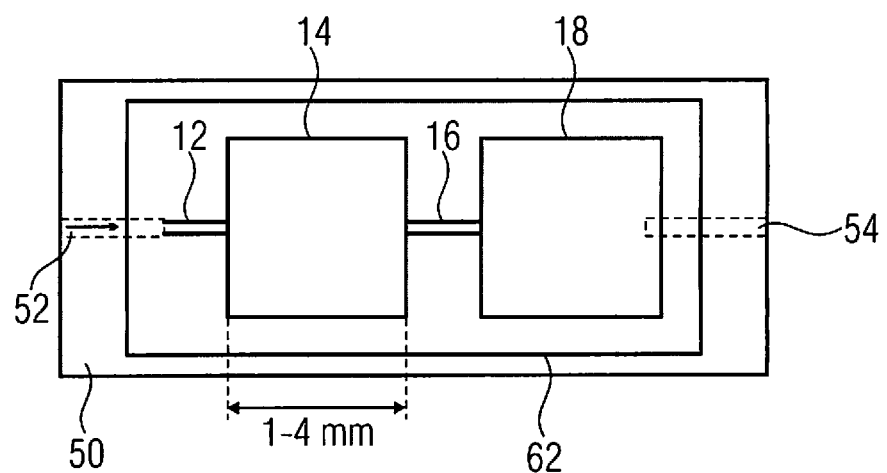

In the top view in FIG. 3*b*, the diaphragm 56 has been omitted in order not to conceal the underlying structures, the recess in the module body 50 into which the diaphragm is inserted being designated by the reference numeral 62.

The flow resistances of the flow restrictions 12 and 16 may also have mutually different sizes, i.e. different flow cross-sections and restriction lengths.

The flow restrictions are designed such that with the flows that occur in normal operation, a pressure drop will occur, so that due to the pressure drop across the flow restriction 16, the second diaphragm section 56*b* is deflected to a lesser degree than the first diaphragm section 56*a*. As compared to the flow restrictions, the measurement areas 14 and 18 have such flow cross-sections that a pressure drop across same is negligible. For example, the flow resistances may be configured such that a pressure drop across any of the flow restrictions in normal operation is at least 10 times to 200 times larger than a pressure drop across any of the measurement chambers.

In embodiments of the invention, the module body 50 may be formed of plastic. The elastic diaphragm may be formed of any suitable material, for example silicone or rubber, and may be joined to the module body, e.g., by means of laser welding, thermocompression welding, ultrasound welding, solvent bonding or other types of bonding. The inlet 52 and the outlet 54 may be formed to be connected to connecting leads, for example infusion conduits, in a simple manner. Corresponding connecting means, e.g. LUER connectors, may be provided.

The fluidic module may thus be implemented as an inexpensive disposable part and enables—as will be explained below—both determining a flow rate and detecting occlusions by detecting the deflections of the two diaphragm sections 56*a* and 56*b*. In order to merely provide an indication of proportions in embodiments of the invention, the length of the measurement chamber 14 may be 1 to 4 mm, as is indicated in FIG. 2*b*.

Figure 4A:
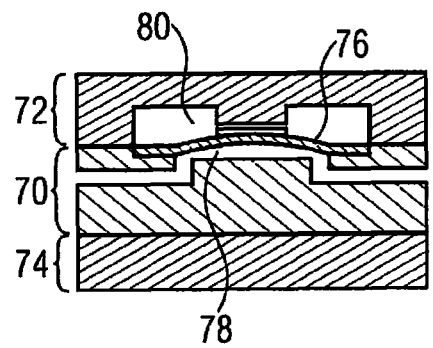
FIGS. 4a to 4c show schematic representations of pressure sensors.
Figure 4B:
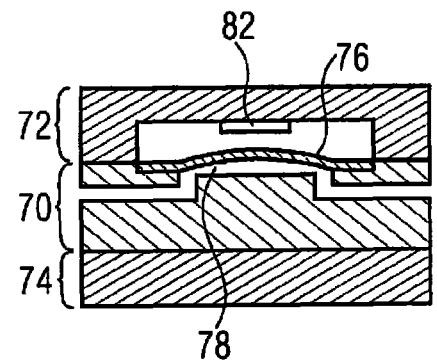
Figure 4C:
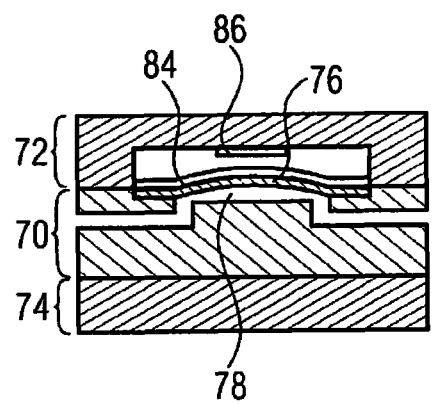

In embodiments of the invention, the diaphragm position may be measured by a detection module, which may be reusable. The position may be measured in different ways, three exemplary possibilities being depicted in FIGS. 4*a* to 4*c*. FIGS. 4*a* to 4*c* each show schematic portions of a fluidic module that are designated by the reference numeral 70. The portions 70 may be part of a disposable module, whereas it is possible for those portions that are designated by references numerals 72 and 74 to be parts of a reusable detector module. FIGS. 4*a* to 4*c* are only illustrative of possibilities of detecting the position of a respective diaphragm 76 arranged above a measurement chamber 78, so that the deflection of the diaphragm 76 is a measure of a pressure existing within the measurement chamber 78.

In accordance with FIG. 4*a*, detection is performed via mechanical switches that are configured to acquire a quantitative measure of the deflection of the diaphragm.

In accordance with FIG. 4*b*, an optical sensor 82, for example in the form of a reflection light barrier, is provided in order to detect the deflection of the diaphragm 76.

In accordance with FIG. 4*c*, capacitive measurement of the deflection of the diaphragm is performed; to this end, an electrode layer 84 is provided on the elastic diaphragm 76, and a counter electrode 86 is provided on the detector module portion 72, so that the two electrodes enable capacitive measurement.

In embodiments of the invention, the sensors thus enable detection of deflection of the diaphragm sections 56*a* and 56*b* as measures of the pressures existing within the measurement chambers 14 and 18.

The relationship between the existing pressure underneath the measurement diaphragms and the deflections of the diaphragm is, in the case of small pressures, proportional to the pressure, and with relatively large deflections, deviations from linearity may arise. However, this function between pressure and deflection is steadily monotonically increasing and may thus be simply batch- or individually calibrated and electronically processed within the detection module.

With batch or individual calibration of the disposable modules, the calibration parameters may be documented on the disposable part, e.g. using a bar code, and may then be read out, during assembly, from said bar code using the detection module, for example in an optical manner.

Figure 5:
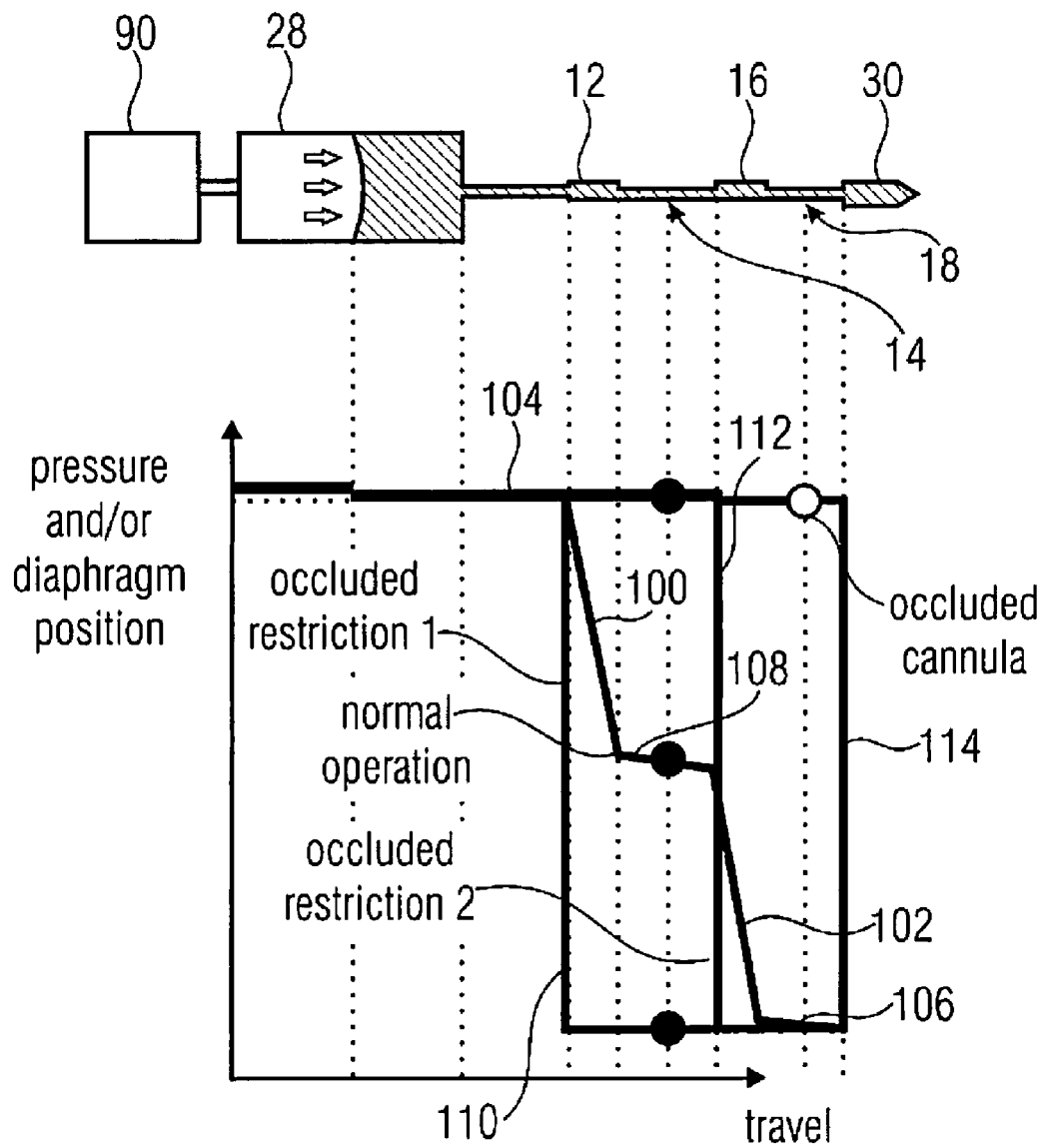
FIG. 5 shows a schematic representation for illustrating the mode of operation of embodiments of the invention.

With regard to FIG. 5 an explanation shall now be given of how one may draw conclusions from the detected pressure and/or diaphragm position with regard to possible occlusions. To this end, the pumping device 28 and the fluidic series connection of the first flow restriction 12, the first measurement chamber 14, the second flow restriction 16, and the second measurement chamber 18 are schematically depicted in the upper part of FIG. 5. One can also recognize that the second measurement area 18 may be provided to immediately adjoin a cannula 30. Finally, a fluid reservoir 90 that may serve to fill up the pumping means 28 is schematically depicted in FIG. 5.

In the lower part of FIG. 5, the pressure and/or the diaphragm positions are depicted for different operating states.

In normal operation, i.e. when there is no occlusion, a pressure drop 100 takes place across the first flow restriction 12, and a pressure drop 102 takes place across the second flow restriction 16. Thus, the pressure existing in the measurement area 14 is between a pressure 104 existing upstream from the first flow restriction 12 and a pressure 106 existing in the second measurement area 18. If the flow restrictions 12 and 16 are identical, the pressure 108 existing in the first measurement area 14 is halfway between the pressures 104 and 106.

If the first flow restriction 12 is occluded, the pressure existing in both measurement areas 14 and 18 will be identical at a low level, which essentially corresponds to the level 106, see curve 110 in FIG. 5. If the flow restriction 14 is occluded, the pressure existing in the measurement area 18 will be essentially at the low level 106, whereas the pressure in the measurement area 14 will be essentially at the high level 104, see curve 112 in FIG. 5. If the cannula 30 is occluded, both measurement chambers 14 and 18 will be essentially at the high level 104, see curve 114 in FIG. 5. Just like an occlusion of the restriction 1, failure of the pumping means would result in that the pressure within both measurement chambers 14 and 18 is essentially at the low level 106.

The inventive arrangement of flow restrictions and measurement areas thus reliably enables detection of any states of occlusion. In particular, even an occlusion of the patient port may be detected without any delay if the device is mounted immediately upstream from a patient port.

The evaluation means may be configured, for example, to compare the detected pressure measures with one another and/or with target values so as to infer the present flow state on the basis of the results of such comparisons. If both measures are at a high level, the evaluation means will determine that the cannula is occluded. If both measures are at a low level, the evaluation means will determine that the first flow restriction is occluded. If the first measure is at a high level and the second measure is at a low level, the evaluation means will determine that the second flow restriction is occluded. If the first measure is at a medium level and the second measure is at a low level, the evaluation means will determine that there is no occlusion, since normal operation is detected.

In addition, the inventive arrangement enables determining a quantitative measure of the flow when the difference of the diaphragm positions is determined—said difference being detected by the sensors 20 and 22—since the flow resistance of the flow restriction, or the geometric dimensions of same, between the two sensors is known. The flow rate, or dosing rate, Q is determined to be:

$$Q = \frac{1}{C_R} \cdot \frac{A^2}{\eta L} \cdot \Delta p$$

$C_R$ represents the form factor of the cross-section of the second flow restriction, A represents the cross-section of the second flow restriction, η represents the viscosity of the flowing fluid, L represents the length of the second flow restriction, and $\Delta p$ represents the pressure drop across the second flow restriction. The pressure drop $\Delta p$ results from the measures, detected by the sensors 20 and 22, of the pressures in the measurement areas 14 and 18. The form factor $C_R$, the cross-section A and the length L are thus specified by and known from the geometry of the second flow restriction, and the pressure drop $\Delta p$ may be determined, for example, from diaphragm positions measured by reflection light barriers. Thus, with reproducible production of the geometry of the second flow restriction, the flow rate may be determined in a reliable and accurate manner.

The measurement area of the flow sensor may be adapted within wide ranges simply in that the cross-sectional area A of the second flow restriction is varied. It may be advantageous for the flow resistance of the first flow restriction to correspond to the flow resistance of the second flow restriction, so that the pressure existing between the flow restrictions is halfway between the pressures existing upstream and downstream from the restrictions. In case of a different mutual relationship of the flow resistances of the flow restrictions, this pressure will be shifted toward the one or other pressure.

Figure 6:
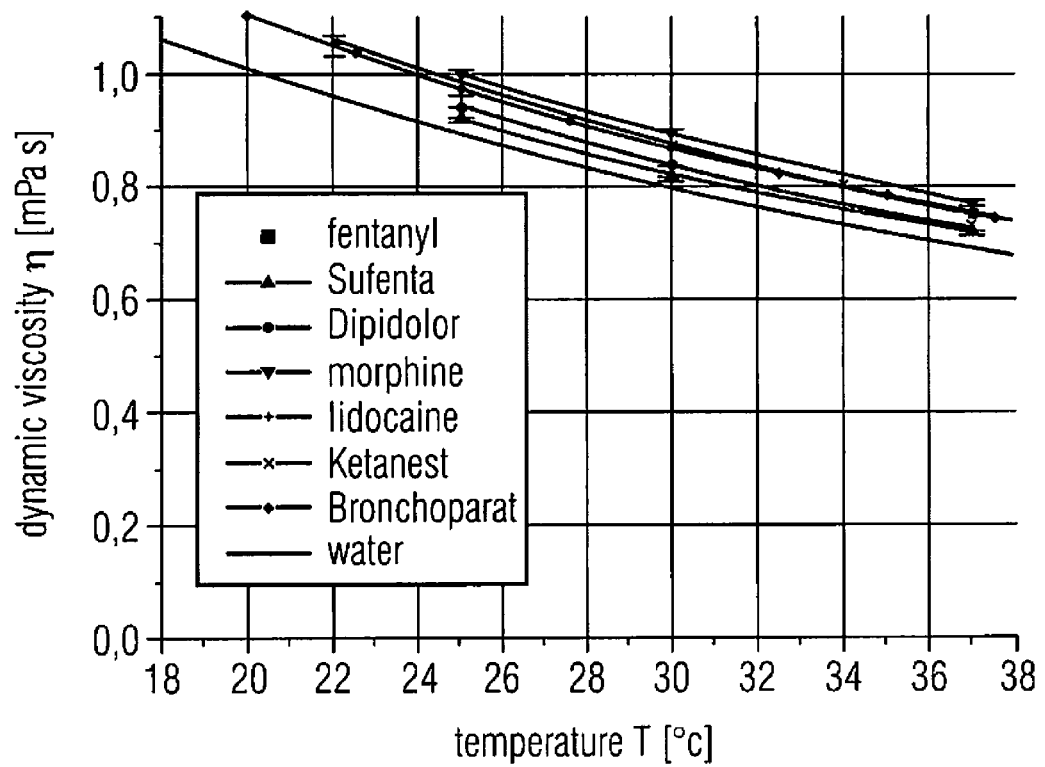
FIG. 6 shows a graphic representation of the temperature dependence of the viscosity of different media.

In embodiments of the present invention, the evaluation means may be configured to determine the flow rate of a fluid flowing through the series connection on the basis of the pressure measurements determined and on the basis of the geometry of the second flow restriction. In embodiments of the invention, the evaluation means may be configured to take into account different viscosities of different media. To this end, the viscosites of different media may be stored as a set of data within a memory of the detection module or of the evaluation means, as was measured, for example, for a series of medicines. The viscosities of medicines are not only slightly different, but also dependent on temperature. In embodiments of the invention, the detection module may thus additionally contain a temperature sensor which compensates for the temperature dependence of the viscosity so that the correct dosing rate may be calculated. For this purpose, the viscosities of the different media may be stored in the memory for different temperatures; in order to determine the flow rate, the evaluation means resorts to the most suitable one of the stored viscosities, depending on the temperature detected by the temperature sensor. FIG. 6 shows a diagram depicting the dynamic viscosities of different medicines as well as of water for different temperatures. The corresponding values may be stored in a memory, for example in a tabular form, for access on the part of the evaluation means.

In this respect, FIG. 2 schematically shows a temperature sensor 37 arranged within the detector module 40. The temperature sensor 37 may be arranged as close as possible to fluid-carrying areas of the fluidic module so as to detect the temperature of the flowing fluid as accurately as possible. In addition, FIG. 1 schematically shows a memory 33 wherein data reflect the viscosities of different media. In addition, data reflecting the temperatures of different media for different temperatures may be stored in the memory.

Embodiments of the invention comprise a single-use fluidic module and a recyclable detection module, which is reusable. The following points influence the measurement accuracy and thus need to be observed. For example, care should be taken during production of the fluidic module that the flow resistances of the flow restrictions and the diaphragm elasticities have little scattering from element to element, it being possible to calibrate the fluidic module during manufacturing. In order to circumvent individual calibration, highly precise and reproducibly manufacturable glass capillaries or channels that etched in silicon and covered may be integrated as flow restrictions into the fluidic module, for example. When joining the fluidic module into the detection module, care should be taken to ensure that the sensors, for example the reflection light barriers, have a defined distance from the elastic diaphragms. The detection module may be configured such that it enables simple insertion of the fluidic module, which may be configured as a simple plastic part; alignment means may be provided to ensure that the defined distance is adhered to.

In embodiments of the invention, the elastic diaphragms may be configured such that in the case of given pressure drops, they maximally have a deflection which corresponds to the entire measurement area of a reflection light barrier, for example 1 mm. Thus, the measurement resolution for the passage may reach a maximum.

In order to enable that the flow cross-sections of the flow restrictions do not increase due to the pressure applied, the detection module may have a mechanical stop above the restrictions, said stop preventing the elastic diaphragm from bulging out, as was explained above with reference to FIG. 3a. Alternatively, the diaphragm above the restriction might be made of a non-elastic material, which, however, entails drawbacks in terms of increased installation expenditure, increased cost and a risk of leakage.

Figure 7:
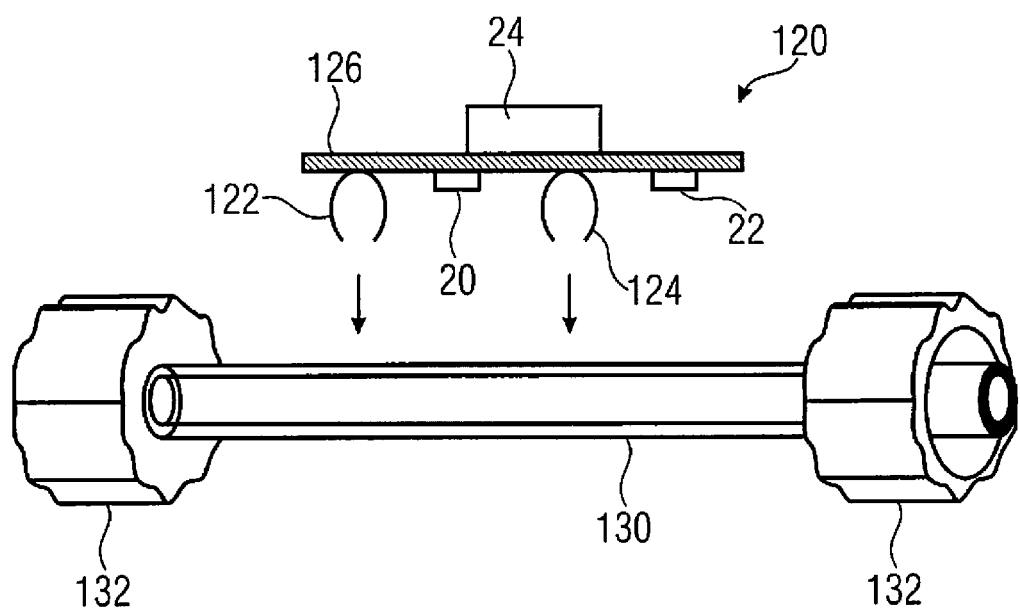
FIG. 7 shows a schematic representation of a further embodiment of the invention.
Figure 8:
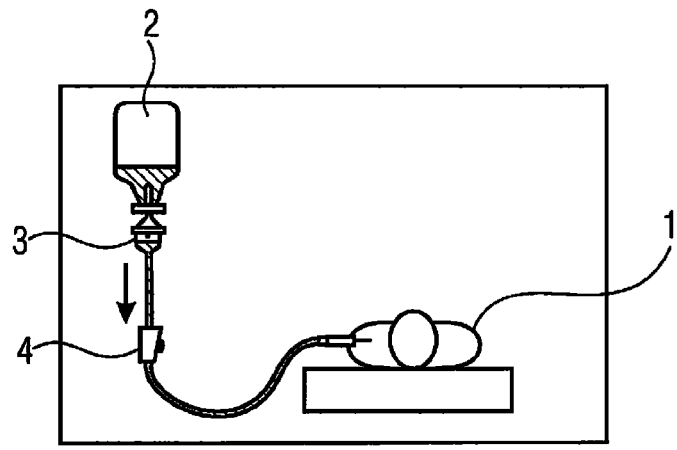
FIG. 8 shows a schematic representation of a gravity infusion in accordance with the prior art.
Figure 9:
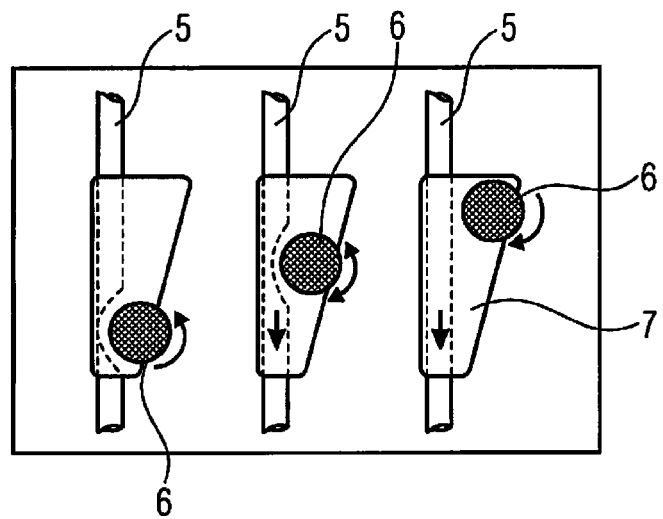
FIG. 9 shows a schematic representation of a roller tubing clamp in accordance with the prior art.

A possible embodiment of a detection module is shown in FIG. 7. The detection module 120 comprises two clips 122 and 124 and two sensors 20 and 22, which may be mounted on a carrier 126 along with an evaluation means 24, said carrier 126 being schematically depicted in FIG. 7 as a plate 126. The detection module 120 may be fitted onto a fluidic conduit 130, such as a tubing having elastic walls. The fluidic conduit 130 may have connecting means 132 on both ends thereof. The clips 122 and 124 are configured such that, by means of the fitting operation, the tubing is compressed by the clips in a defined manner, so that the first and second flow restrictions are formed by the clips 122 and 124. By means of the fitting operation, the sensors 20 and 22, which in turn may be configured as reflection light barriers, are positioned in such a manner in relation to the wall of the fluidic conduit that deflections of the wall may be detected. Fitting the detection module 120 onto the fluid conduit 130 thus again yields a fluidic series connection of the first flow restriction, the first measurement area, the second flow restriction, and the second measurement area.

Alternatively, restrictions and sensors may be configured as individual modules in each case which are fluidically fitted onto one another.

Embodiments of the invention relate to utilization of inventive methods and devices for infusions, such as gravity infusions or syringe infusions. Embodiments of the present invention may thus be implemented by a corresponding infusion apparatus.

While this invention has been described in terms of several embodiments, there are alterations, permutations, and equivalents which fall within the scope of this invention. It should also be noted that there are many alternative ways of implementing the methods and compositions of the present invention. It is therefore intended that the following appended claims be interpreted as including all such alterations, permutations and equivalents as fall within the true spirit and scope of the present invention.

The invention claimed is:

1. A device for determining at least one flow parameter, comprising:
 a fluidic series connection comprising, in this order, a first flow restriction, a first measurement area, a second flow restriction, and a second measurement area;
 a first sensor for detecting a quantitative first measure of the pressure in the first measurement area;
 a second sensor for detecting a second quantitative measure of the pressure in the second measurement area; and
 an evaluator configured to determine, while using the measures detected by the first and second sensors, whether there is an occlusion of the first flow restriction, of the second flow restriction or of a fluid area adjoining the second measurement area.

2. The device as claimed in claim 1, wherein the evaluator is further configured to determine, while using the measures detected by the first and second sensors, a flow rate of a fluid flowing through the series connection.

3. The device as claimed in claim 1, wherein the fluid area adjoining the second measurement area is a cannula.

4. The device as claimed in claim 1, wherein the measurement areas comprise elastic wall areas whose positions depend on the pressures existing in the measurement areas, the sensors being configured to measure the positions of the elastic wall areas.

5. The device as claimed in claim 4, wherein the sensors comprise optical sensors, capacitive sensors, or mechanical switches.

6. The device as claimed in claim 1, wherein the fluidic series connection comprises structures within a fluidic module body that are covered by a flexible diaphragm at least in the measurement areas.

7. The device as claimed in claim 6, wherein the flexible diaphragm extends across the flow restrictions, hold-up elements being provided to prevent the flexible diaphragm from deflecting in the area of the flow restrictions.

8. The device as claimed in claim 1, further comprising a temperature sensor, the evaluator being configured to take into account a temperature dependence of the viscosity of the fluid flowing through the fluidic series connection when determining the flow rate.

9. The device as claimed in claim 8, further comprising a memory, wherein data reflecting the viscosity of one or more fluids is stored.

10. The device as claimed in claim 1, wherein the evaluator is configured to determine that there is an occlusion of the first flow restriction when the first measure and the second measure indicate a pressure that comprises a first, low level at which it is determined that there is an occlusion of the second flow restriction when the first measure comprises a pressure having a second, high level, which is higher than the first, low level, and the second measure indicates a pressure of the low first level, at which it is determined that there is an occlusion of the fluid area adjoining the second measurement area when the first and second measures indicate a pressure of the second, high level, and wherein it is determined that there is no occlusion when the first measure indicates a third pressure which is between the first and second levels, and when the second measure indicates a pressure of a level which lies in the region of the low first level.

11. The device as claimed in claim 1, further comprising a pump for providing a fluid flow through the fluidic series connection, the evaluator being configured to control the pump on the basis of the measures detected so as to achieve a desired flow rate.

12. The device as claimed in claim 1, wherein the fluidic series connection is formed within a fluidic module which may be exchangeably coupled to one or more modules that comprise the first and second sensors and the evaluator.

13. The device as claimed in claim 1, wherein the first and second flow restrictions are implemented by compressed areas of an elastic tubing, and the measurement areas are implemented by non-compressed areas of the elastic tubing.

14. A fluidic module for a device as claimed in claim 12, comprising:
 a module body having a structured module body surface; and
 a diaphragm mounted on the module body and defining a fluid area together with the structured module body surface, the fluid area comprising a first flow restriction, a first measurement chamber adjoining the first flow restriction, a second flow restriction adjoining the first measurement chamber, and a second measurement chamber adjoining the second flow restriction.

15. The fluidic module as claimed in claim 14, wherein an inlet channel fluidically connected to the first flow restriction and an outlet channel fluidically connected to the second measurement chamber are formed within the module body.

16. The fluidic module as claimed in claim 15, wherein the inlet channel and the outlet channel end in mutually opposite side faces of the module body.

17. A detection module for a device as claimed in claim 13, which may be fitted onto the elastic tubing, comprising:
 a first clamping device for clamping the detection module onto the elastic tubing at a first position alongside the elastic tubing;
 a second clamping device for clamping the detection module onto the elastic tubing at a second position alongside the elastic tubing, said second position being spaced apart from the first position,
 the first and second clamping devices being configured to compress the elastic tubing in a defined manner in each case so as to define the first and second flow restrictions;
 the first sensor, which is configured to detect a measure of the pressure existing between the first and second flow restrictions within the elastic tubing; and
 the second sensor, which is configured to measure a measure of the pressure existing within a tubing area arranged on a side of the second flow restriction that faces away from the first flow restriction.

18. A method of determining at least one flow parameter, comprising:

introducing a fluid into a fluidic series connection comprising, in this order, a first flow restriction, a first measurement area, a second flow restriction, and a second measurement area, detecting a quantitative first measure of a pressure in the first measurement area, and detecting a quantitative second measure of a pressure in the second measurement area; and determining whether an occlusion of the first flow restriction, of the second flow restriction or of a fluid area adjoining the second measurement area is present while using the detected quantitative first and second measures.

19. The method as claimed in claim 18, further comprising determining a flow rate of the fluid while using the quantitative first and second measures detected.

20. The method as claimed in claim 18, wherein for determining the flow rate, a temperature and a temperature dependence of the viscosity of the fluid are taken into account.

21. The method as claimed in claim 18, comprising determining that there is an occlusion of the first flow restriction when the first measure and the second measure indicate a first, low pressure level at which it is determined that there is an occlusion of the second flow restriction when the first measure indicates a second, high pressure level, which is higher than the first, low level, and the second measure indicates the low first pressure level, at which it is determined that there is an occlusion of the fluid area adjoining the second measurement area when the first and second measures indicate the second, high pressure level, and wherein it is determined that there is no occlusion when the first measure indicates a third pressure level which is between the first and second pressure levels, and when the second measure indicates a pressure level which lies in the region of the low first pressure level.

22. The method as claimed in claim 18, further comprising controlling a pump while using the detected first and second measures so as to effect a desired flow rate through the fluidic series connection.

23. An infusion apparatus comprising a device as claimed in claim 1.

24. An infusion apparatus comprising a fluidic module as claimed in claim 14.

25. An infusion apparatus comprising a detection module as claimed in claim 17.

* * * * *